United States Patent
Desi Reddy et al.

(10) Patent No.: US 11,312,743 B1
(45) Date of Patent: Apr. 26, 2022

(54) PROCESS FOR MOLNUPIRAVIR

(71) Applicant: OPTIMUS DRUGS PRIVATE LIMITED, Telangana (IN)

(72) Inventors: Srinivas Reddy Desi Reddy, Hyderabad (IN); Subba Reddy Peketi, Hyderabad (IN); Venkata Gnaneswara Rao Guttikonda, Hyderabad (IN); Siva Reddy Desi Reddy, Hyderabad (IN)

(73) Assignee: Optimus Drugs Private Limited, Telangana (IN)

( * ) Notice: Subject to any disclaimer, the term of this patent is extended or adjusted under 35 U.S.C. 154(b) by 0 days.

(21) Appl. No.: 17/383,405

(22) Filed: Jul. 22, 2021

(30) Foreign Application Priority Data

Mar. 20, 2021 (IN) .............................. 202141011933

(51) Int. Cl.
*C07H 19/067* (2006.01)
*C07H 1/00* (2006.01)
(52) U.S. Cl.
CPC ............. *C07H 19/067* (2013.01); *C07H 1/00* (2013.01)

(58) Field of Classification Search
None
See application file for complete search history.

(56) References Cited

FOREIGN PATENT DOCUMENTS

WO WO-2021137913 A2 * 7/2021 ............. C07H 19/16

OTHER PUBLICATIONS

Greene, "Protection for the Hydroxyl Group, Including 1,2-and 1,3-Diols," Protective Groups in Organic Synthesis, Third Edition, 1999 John Wiley & Sons, Inc., pp. 17-245. (Year: 1999).*
Gopalsamuthiram, Synlett 32(03):326-328, Feb. 2021. (Year: 2021).*

* cited by examiner

*Primary Examiner* — Layla D Berry
(74) *Attorney, Agent, or Firm* — IP Pundit LLC

(57) ABSTRACT

The present invention relates to a process for the preparation of Molnupiravir. The present invention also relates to an improved and commercially viable process for preparation of Molnupiravir with high yield and purity.

3 Claims, No Drawings

PROCESS FOR MOLNUPIRAVIR

CROSS REFERENCE TO RELATED APPLICATIONS

The instant application claims priority to the Indian provisional application number 202141011933, filed on Mar. 20, 2021, the disclosure of all of which is hereby incorporated by reference in its entirety.

FIELD OF THE INVENTION

The present invention relates to a process for the preparation of Molnupiravir. The present invention also relates to an improved and commercially viable process for preparation of Molnupiravir with high yield and purity.

BACKGROUND OF THE INVENTION

Molnupiravir (development codes MK-4482 and EIDD-2801) is an experimental antiviral drug which is orally active and was developed for the treatment of influenza. It is a prodrug of the synthetic nucleoside derivative N4-hydroxycytidine and exerts its antiviral action through introduction of copying errors during viral RNA replication. Activity has also been demonstrated against coronaviruses including SARS, MERS and SARS-CoV-2.

In April 2020, a whistle blower complaint by former Head of US Biomedical Advanced Research and Development Authority (BARDA) Rick Bright revealed concerns over providing funding for the further development of Molnupiravir due to similar drugs having mutagenic properties (producing birth defects). A previous company, Pharmasset, that had investigated the drug's active ingredient had abandoned it. These claims were denied by George Painter, CEO of DRIVE (Drug Innovation Ventures at Emory), noting that toxicity studies on Molnupiravir had been carried out and data provided to regulators in the US and UK, who permitted safety studies in humans to move forward in the spring of 2020. Also at this time, DRIVE and Ridgeback Biotherapeutics stated they planned future safety studies in animals.

After being found to be active against SARS-CoV-2 in March 2020, Molnupiravir was tested in a preliminary human study for "Safety, Tolerability, and Pharmacokinetics" in healthy volunteers in the UK and US. In June 2020, Ridgeback Biotherapeutics announced it was moving to Phase II trials to test the efficacy of the drug as a treatment for COVID-19. Two trials of small numbers of hospitalized and non-hospitalized patients in the US and the UK were underway in July. In late July 2020, and without yet releasing any medical data, Merck, which had been partnering with Ridgeback Biotherapeutics on developing the drug, announced its intention to move Molnupiravir to late-stage trials beginning in September 2020. On Oct. 19, 2020, Merck began a one-year Stage 2/3 trial focused on hospitalized patients.

The study found that the drug was "efficacious" when administered orally to infected ferrets, and that it blocked the transmission of the virus between ferrets after 24 hours following administration of the drug. Molnupiravir structural formula is as follows:

MOLNUPIRAVIR (I)

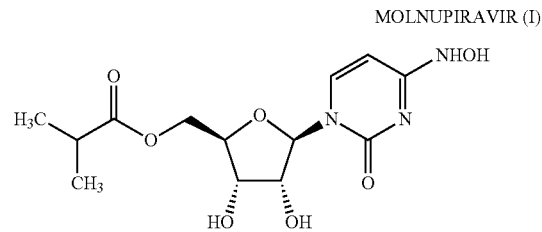

Molnupiravir is reported in US 20200276219 ("US'219") assigned to Emory University. The synthetic process for Molnupiravir is reported in US'219 comprises reacting Uridine (VI) with acetone in presence of $H_2SO_4$/TEA to obtain the compound of formula (VII). The compound of formula (VII) is reacted with 2-methylpropanoyl 2-methyl propanoate in presence of TEA/4-DMAP and EtOAc to obtain the compound of formula (VIII). The compound of formula (VIII) is reacted with 1,2,4-triazole in presence of MeCN/N,N-diethylethanamine/$POCl_3$/$H_2O$ and MDC to obtain the compound of formula (IX). The compound of formula (IX) is reacted with $NH_2OH$ in presence of IPA/EtOAc and $H_2O$ to obtain the compound of formula (V). The compound of formula (V) deprotected with HCOOH in presence of MTBE/IPA to obtain Molnupiravir (I).

The above process is schematically shown as below:

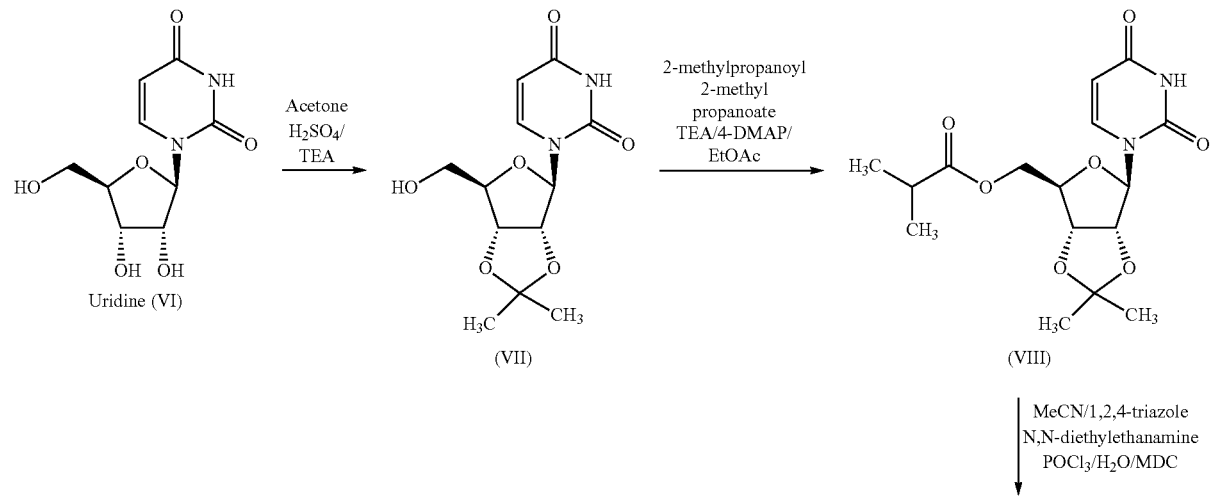

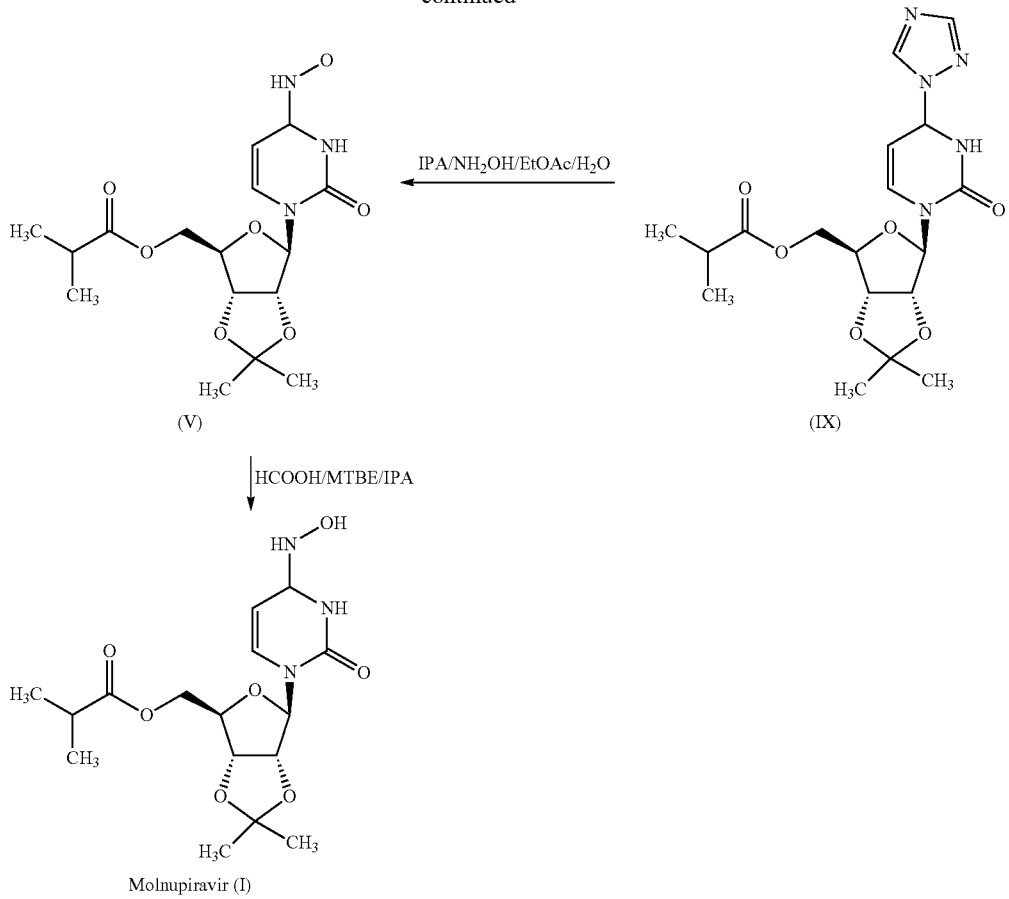

Gopalsamuthiram et al. ("A Concise Route to MK-4482 (EIDD-2801) from Cytidine: Part 2" Synlett (2021), 32(3), 326-328) discloses a process for the preparation of Molnupiravir (I), wherein Cytidine (II) is reacted with 2,2-dimethoxypropane in presence of acetone and $H_2SO_4$ to obtain 2',3'-O-(1-methylethylidene)-sulfate Cytidine (III). The compound of formula (III) is reacted with isobutyric anhydride in presence of DBU/DMAP/MeCN/EtOAc/$H_2O$ and sodium bicarbonate to obtain 2',3'-O-(1-methylethylidene)-5'-(2-methyl propanoate) Cytidine (IV). The compound of formula (IV) is reacted with $NH_2OH.H_2SO_4$ in presence of IPA/$H_2O$/EtOAc/$NaHCO_3$ and toluene to obtain 2',3'-O-(1-methylethylidene)-4-oxime-5'-(2-methyl propanoate) Uridine (V). The compound of formula (V) deprotected with $HCO_2H$ to obtain Molnupiravir (I).

The above process is schematically shown as below:

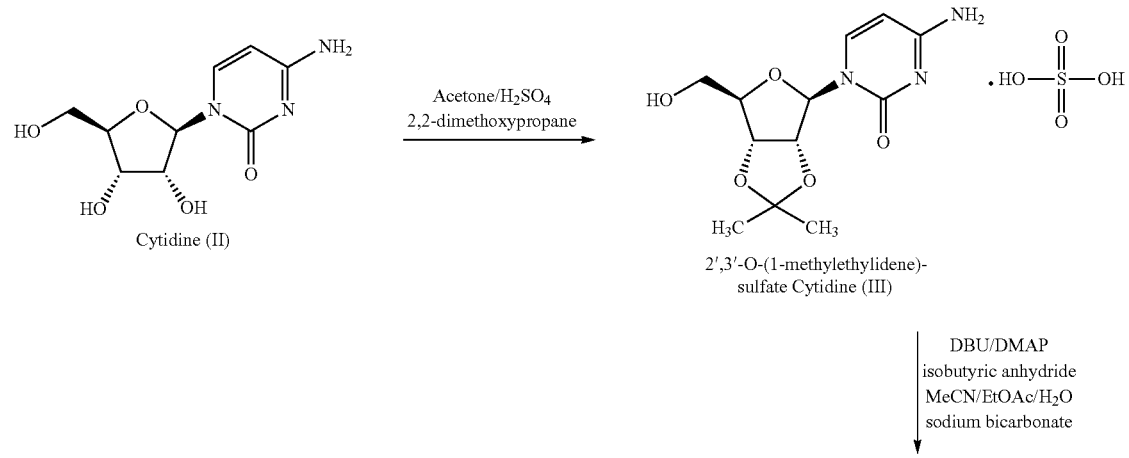

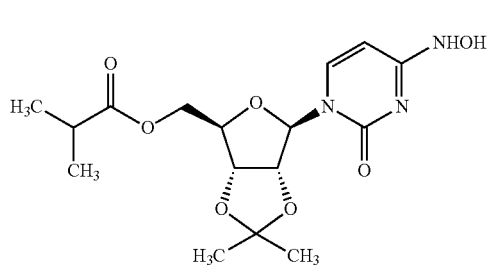

2',3'-O-(1-methylethylidene)-4-oxime-5'-
(2-methylpropanoate) Uridine (V)

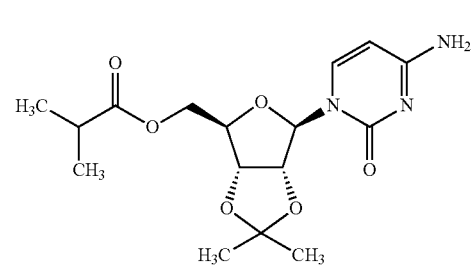

2',3'-O-(1-methylethylidene)-5'-(2-
methyl propanoate) Cytidine (IV)

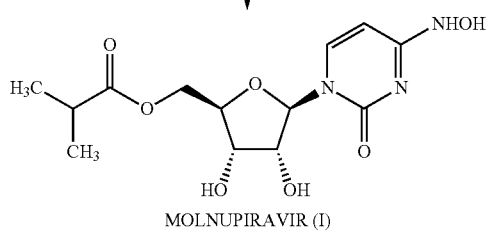

MOLNUPIRAVIR (I)

The main drawback of the prior art is that the processes for the preparation of Molnupiravir described thus far are associated with low yield and low purity. Further, the processes described in the prior art require conversion of 2',3'-O-(1-methylethylidene)-4-oxime-5'-(2-methyl propanoate) Uridine (V) to crude Molnupiravir in presence formic acid ($HCO_2H$). Furthermore, the processes include a step of purifying crude compound of Molnupiravir using silica gel column chromatography in 8% $MeOH/CHCl_3$ to obtain Molnupiravir (I). Hence, the number of steps requires various techniques to get a purified compound and with less yield and purity.

The advantage of the present invention is process for the preparation of Molnupiravir with high yield and high purity. In view of the foregoing, the present invention provides as result of extensive studies, process for the preparation of Molnupiravir (I) from 2',3'-O-(1-methylethylidene)-4-oxime-5'-(2-methyl propanoate) Uridine (V) in presence of trifluoroacetic acid or hydrochloric acid in suitable organic solvents and temperatures.

SUMMARY OF THE INVENTION

The present invention relates to a process for the preparation of Molnupiravir. The present invention also relates to an improved and commercially viable process for preparation of Molnupiravir with high yield and purity.

The present invention provides a process for the preparation of Molnupiravir (I), comprising the steps of, a) reacting Cytidine (II) with 2,2-dimethoxypropane and $H_2SO_4$ in presence of an organic solvent to obtain compound (III), 2',3'-O-(1-methylethylidene)-sulfate Cytidine,

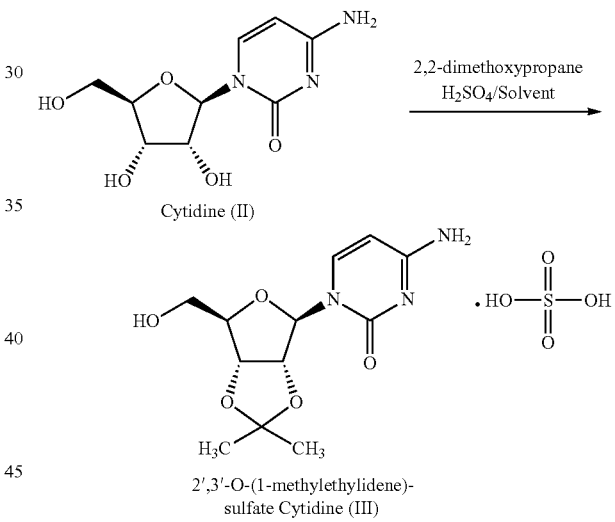

b) reacting compound (III) with isobutyric anhydride in presence of an organic base and an organic solvent at a temperature of 0-5° C. for 60 min, to obtain compound (IV), 2',3'-O-(1-methylethylidene)-5'-(2-methyl propanoate) Cytidine,

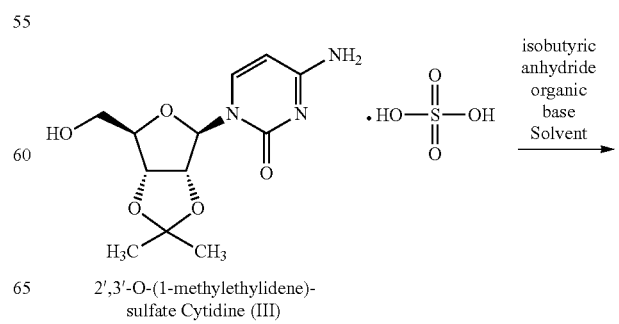

-continued

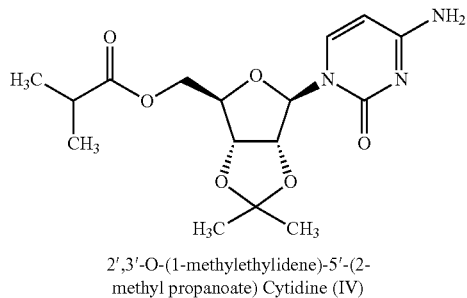

2',3'-O-(1-methylethylidene)-5'-(2-methyl propanoate) Cytidine (IV)

c) reacting compound (IV) with hydroxylamine sulfate in presence of an organic solvent to obtain compound (V), 2',3'-O-(1-methylethylidene)-4-oxime-5'-(2-methyl propanoate) Uridine,

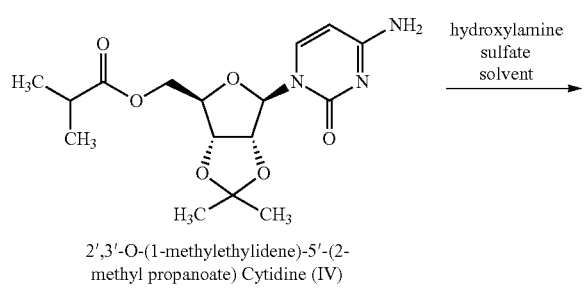

2',3'-O-(1-methylethylidene)-5'-(2-methyl propanoate) Cytidine (IV)

2',3'-O-(1-methylethylidene)-4-oxime-5'-(2-methylpropanoate) Uridine (V)

d) deprotecting compound (V) with trifluoroacetic acid or hydrochloric acid in presence of an organic solvent and water, at a temperature of 50-55° C. for about 2-3 hours, to obtain Molnupiravir (I), and

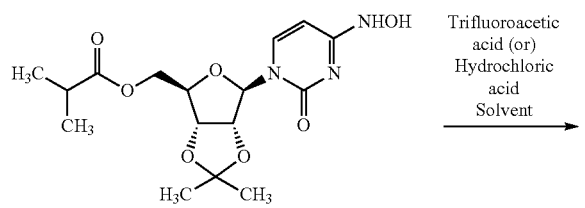

2',3'-O-(1-methylethylidene)-4-oxime-5'-(2-methylpropanoate) Uridine (V)

-continued

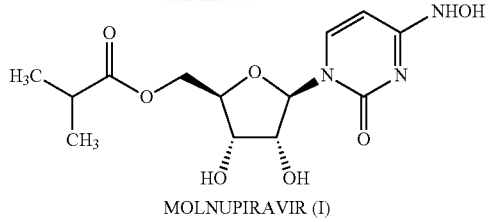

MOLNUPIRAVIR (I)

e) isolating Molnupiravir (I).

DETAILED DESCRIPTION OF THE INVENTION

The present invention relates to a process for the preparation of Molnupiravir. The present invention also relates to an improved and commercially viable process for preparation of Molnupiravir with high yield and purity.

The present invention provides a process for the preparation of Molnupiravir (I), comprising the steps of,
a) reacting Cytidine (II) with 2,2-dimethoxypropane and $H_2SO_4$ in presence of an organic solvent to obtain the compound (III), 2',3'-O-(1-methylethylidene)-sulfate Cytidine,
b) reacting compound (III) with isobutyric anhydride in presence of an organic base and an organic solvent at a temperature of 0-5° C. for 60 min, to obtain compound (IV) 2',3'-O-(1-methylethylidene)-5'-(2-methyl propanoate) Cytidine,
c) reacting the compound of formula (IV) with hydroxylamine sulfate in presence of an organic solvent to obtain compound (V), 2',3'-O-(1-methylethylidene)-4-oxime-5'-(2-methyl propanoate) Uridine,
d) deprotecting compound (V) with trifluoroacetic acid or hydrochloric acid in presence of an organic solvent and water, at a temperature of 50-55° C. for about 2-3 hours, to obtain Molnupiravir (I), and
e) Isolating Molnupiravir (I).

In an embodiment of the present invention, Cytidine (II) is reacted with 2,2-dimethoxypropane and $H_2SO_4$ in presence of acetone to obtain compound (III), 2',3'-O-(1-methylethylidene)-sulfate Cytidine. In one aspect of the embodiment, compound (III) is reacted with isobutyric anhydride in presence of DBU/DMAP/acetonitrile at 0-5° C. for 60 min to obtain compound (IV), 2',3'-O-(1-methylethylidene)-5'-(2-methyl propanoate) Cytidine. In another aspect of the embodiment, compound (IV) is reacted with hydroxylamine sulfate in presence of isopropyl alcohol and water by Karl Fisher titration at 70-80° C. for 17-18 hours to obtain compound (V), 2',3'-O-(1-methylethylidene)-4-oxime-5'-(2-methyl propanoate) Uridine. In another aspect of the embodiment, compound (V) is deprotected with trifluoroacetic acid or hydrochloric acid in presence of an organic solvent and water at 25-60° C. for 2-3 hours, preferably 50-55° is maintained for about 2-3 hours, wherein the reaction mass pH is maintained between 7.0-10.0 by using sodium carbonate solution to obtain Molnupiravir (I).

In another aspect of the embodiment, the amount of isobutyric anhydride used in the range of about 0.05 to 1 mole, more preferably 0.55 to 0.57 moles; the amount of DBU used in the range of about 0.5 to 1.5 moles, more preferably 1.06 to 1.16 moles; the amount of DMAP used in the range of about 0.01 to 1 mole, more preferably 0.07 to 0.10 moles In another embodiment, the instant application provides purification process for the preparation of Molnupiravir (I), comprising the Molnupiravir purified with organic solvent and the reaction is carried out at 70-80° C. for 10-15 min to obtain pure Molnupiravir (I).

According to one embodiment the Molnupiravir (I) obtained using a process described herein is ≥99.5% pure, measured using HPLC.

According to another embodiment of the present invention, the organic solvent is selected from the group consisting of acetone, acetonitrile, ethyl acetate, water, isopropyl alcohol, methanol, ethanol, toluene, dimethyl sulfoxide (DMSO), dimethylformamide (DMF), isopropyl acetate and n-butyl acetate, methyl ethyl ketone, methyl isobutyl ketone, cyclohexanone, diethyl ether, di isopropyl ether, dioxane, tetrahydrofuran, 1,2-dimethoxyethane, dichloromethane (MDC), dichloroethane, carbon tetrachloride and chloroform and/or mixtures thereof.

According to yet another embodiment of the present invention, the organic base is selected from 1,8-diazabicyclo [5.4.0] undec-7-ene (DBU), Dimethyl aminopyridine (DMAP), 5-diazabi cyclo[4.3.0]non-5-ene (DBN), pyridine, triethylamine (TEA), Diisopropylethylamine (DIPEA), trimethylamine, diethylamine and N,N-dimethylaniline.

The following examples illustrate the present invention but should not be construed as limiting the scope of the invention.

EXAMPLES

Example-1: Preparation of 2',3'-O-(1-methylethylidene)-sulfate Cytidine (III)

Acetone (100 ml), cytidine (10 gm) and 2,2-dimethoxypropane (30 ml) were added into RB (round bottom) Flask, followed by addition of sulphuric acid (4 ml) into flask at below 30° C., stir the mass at 25-30° C. for 4-5 hours. After completion of the reaction, filter the resultant solid material, wash with acetone (30 ml) and dry for 20 min. The obtained crude wet material into RB Flask, added ethyl acetate (70 ml) and Stir the mass for 60 min at 25-30° C. The resultant solid was washed with ethyl acetate (30 ml) and dry for 20 min. to get off white colour compound.
Yield: 30 gms
Purity: 99.02%

Example-2: Preparation of 2',3'-O-(1-methylethylidene)-5'-(2-methyl propanoate) Cytidine (IV)

Charge acetonitrile (75.0 ml), 2',3'-O-(1-methylethylidene)-sulfate cytidine (30.0 gm) and 1,8-Diazabicyclo [5.4.0]undec-7-ene (DBU) (12.75 ml) into RB flask at 25-30° C. Stir the reaction mass for 10 min to get a clear solution, further added 4-Dimethylamino pyridine (DMAP) (0.75 gm) into flask, cool the mass to 0-5° C., slowly add isobutyric anhydride (6.9 ml) to the reaction mass at 0-5° C. and stir for 60 min. After completion of the reaction, charge purified water (150 ml) and dichloromethane (105 ml) to the reaction mass, Stir for 10 min to separate the layers, extracted dichloromethane layer was washed with 10% sodium bicarbonate solution (30 ml). The separated organic layer (MDC Layer) was concentrated under reduced pressure at below 50° C. to get title compound.
Yield: 95.17% (13.8 gms)
Purity: 92.73%

Example-3: Preparation of 2',3'-O-(1-methylethylidene)-4-oxime-5'-(2-methyl propanoate) Uridine (V)

Charge isopropyl alcohol (145 ml), purified water (41.4 ml), 2',3'-O-(1-methylethylidene)-5'-(2-methyl propanoate) Cytidine (13.8 gm) and hydroxylamine sulphate (17.25 gm) into RB flask at 25-30° C. The reaction mass temperature raised to 70-80° C. and maintain for 17-18 hours. After completion of the reaction, concentrate the mass under reduced pressure at below 70° C. and allow to cool at below 30° C. Charge purified water (138 ml) and 10% sodium carbonate solution into flask, stir for 60 min. The obtain material was filtered, wash with purified water (27.6 ml) and suck dry for 10 min, followed by addition of toluene (13.8 ml) and the reaction mixture was allowed to cool at 0-5° C. and stir for 30 min. The resultant material was filtered, washed with toluene (2.76 ml) and dry the material for 8 hours at 55-60° C. to get off white colour solid compound.
Yield: 80.12% (11.5 gm)
Purity: 96.81%

Example-4: Preparation of Molnupiravir (I)

2',3'-O-(1-methylethylidene)-4-oxime-5'-(2-methyl propanoate), Uridine (10 gm) and purified water (10 ml) were added into RB flask at room temperature, followed by addition of trifluoroacetic acid (30 ml) at below 35° C. The reaction mass was allow to stir for 2 hours at 50-55° C. After completion of the reaction, the reaction mass was concentrated under reduced pressure at below 55° C. and allow to cool the mass at 25-30° C., Quench the reaction mass with 30% sodium carbonate solution (50 ml) at same temperature and stir for 60-120 min, further cool to 0-5° C. and stir for 20-30 min. The resultant material was filtered, washed with purified water (2 ml), ethyl acetate (5 ml) and dry the material at 60-65° C. to get Molnupiravir.
Yield: 69.66% (6.2 gms)
Purity: 97.79%

Example-5: Preparation of Molnupiravir (I)

Charge Ethyl acetate (100 ml), 2',3'-O-(1-methylethylidene)-4-oxime-5'-(2-methyl propanoate) Uridine (10.0 gm) and purified water (1.0 ml) into RBF, followed by addition of hydrochloric acid (2.70 gm) at 25-30° C. and allow to stir at 50-55° C. for 2-3 hours. After completion of the reaction, Cool the mass temperature to 25-30° C., adjust the reaction mass pH to 7.5-8.5 with 10% Sodium carbonate solution (50.0 ml) and stir for 15-20 min to separate the two layers. The obtain ethyl acetate layer was wash with 30% sodium chloride solution and water (20 ml), further it was charged with activated carbon (0.2 gm), stir for 10-15 min at room temperature and filter the mass through hyflo bed. The filtrate (ethyl acetate layer) was concentrated under vacuum at below 60° C. under reduced pressure and degas the mass at the same temperature under vacuum for 60 min. The resultant material was washed with ethyl acetate (10.0 ml) and dried at 60-65° C. for 8-10 hours to obtain 7.50 gm of the pure material.
Yield: 84.26% (7.50 gm)
Purity: 99.9%

Example-6: Purification of Molnupiravir

Crude Molnupiravir material (91.0 gm) were added to isopropyl alcohol (600 ml), stir the mass at 70-80° C. for 10-15 min to dissolve the material. Charge activated carbon (5.0 gm) and stir for 10 min at the same temperature. The reaction mass was filter through hyflo bed and wash with isopropyl alcohol (100 ml). The reaction mass was concentrated under reduced pressure at below 60° C., further added purified water (200 ml) and stir for 10-15 min at 60-65° C.

The reaction mass was allow to 0-5° C. and stir for 30-60 min at the same temperature. The resultant material was filter, washed with chilled purified water (25 ml) and dried at 60-65° C. to get pure Molnupiravir.

Yield: 68.08% (60.6 gm)
Purity: 99.79%.

We claim:

1. A process for preparation of Molnupiravir (I), comprising:

a) reacting Cytidine (II) with 2,2-dimethoxypropane and H₂SO₄ in presence of organic solvent to obtain compound (III), 2',3'-O-(1-methylethylidene)-sulfate Cytidine,

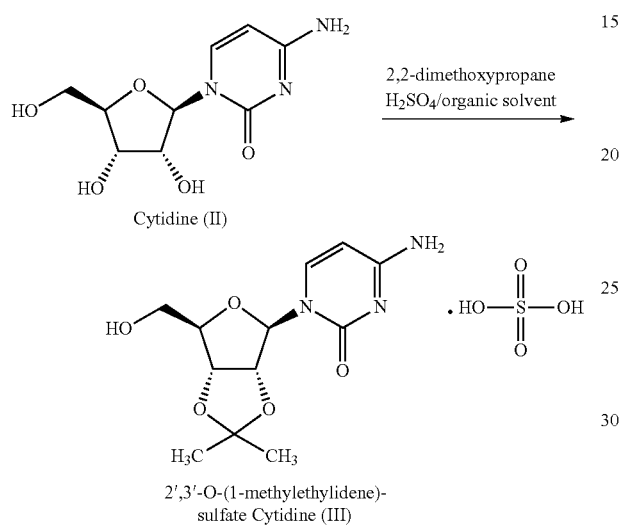

b) reacting compound (III) with isobutyric anhydride in presence of organic base and organic solvent, at a temperature of 0-5° C. for 60 min, to obtain compound (IV), 2',3'-O-(1-methylethylidene)-5'-(2-methyl propanoate) Cytidine,

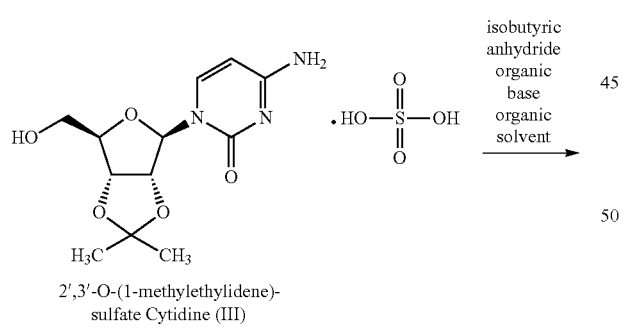

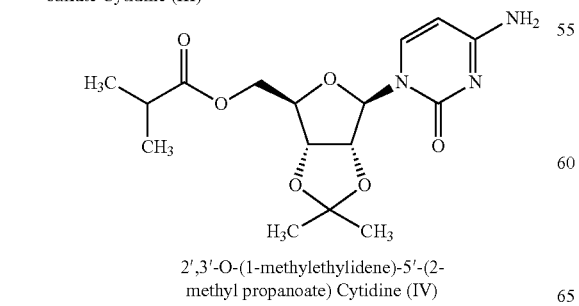

c) reacting compound (IV) with hydroxylamine sulfate in presence of organic solvent to obtain compound (V), 2',3'-O-(1-methylethylidene)-4-oxime-5'-(2-methyl propanoate) Uridine,

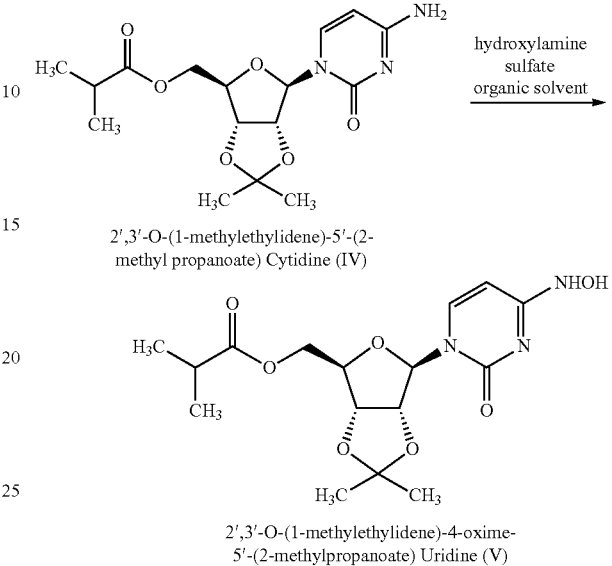

d) deprotecting formula (V) with trifluoroacetic acid or hydrochloric acid in presence of organic solvent and water, at a temperature of 50-55° C. for about 2-3 hours, to obtain Molnupiravir (I), and

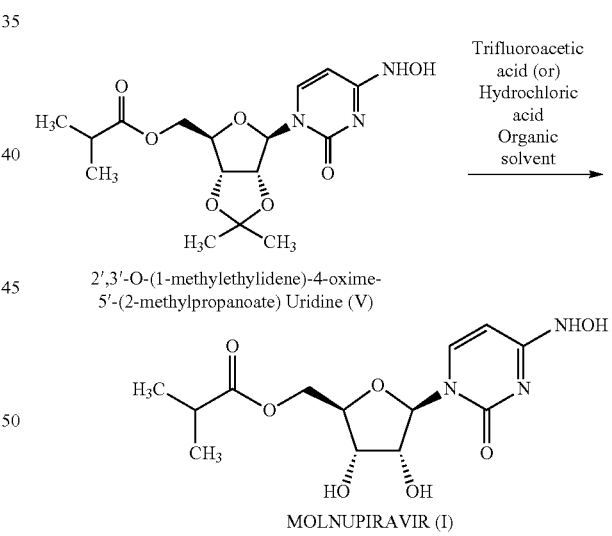

e) isolating the Molnupiravir (I).

2. The process according to claim 1, wherein the organic solvent in step a) is acetone, step b) is acetonitrile, step c) is isopropyl alcohol, and step d) is ethyl acetate.

3. The process according to claim 1, wherein the organic base is selected from the group consisting of 1,8-diazabicyclo [5.4.0] undec-7-ene (DBU), Dimethylaminopyridine (DMAP), 5-diazabi cyclo[4.3.0]non-5-ene (DBN), pyridine, triethylamine (TEA), Diisopropylethylamine (DIPEA), trimethylamine, diethylamine and N,N-dimethylaniline.

* * * * *